(12) United States Patent
Cawthan et al.

(10) Patent No.: US 8,414,586 B2
(45) Date of Patent: Apr. 9, 2013

(54) INSTRUMENT FOR REMOVING BONE TISSUE

(75) Inventors: Simon Cawthan, Leeds (GB); Gary Moore, Leeds (GB)

(73) Assignee: Depuy International Limited (GB)

( * ) Notice: Subject to any disclaimer, the term of this patent is extended or adjusted under 35 U.S.C. 154(b) by 0 days.

(21) Appl. No.: 12/810,114

(22) PCT Filed: Dec. 12, 2008

(86) PCT No.: PCT/GB2008/004098
§ 371 (c)(1),
(2), (4) Date: Jun. 22, 2010

(87) PCT Pub. No.: WO2009/083707
PCT Pub. Date: Jul. 9, 2009

(65) Prior Publication Data
US 2010/0280517 A1    Nov. 4, 2010

(30) Foreign Application Priority Data
Dec. 27, 2007   (GB) .................................. 0725263.8

(51) Int. Cl.
*A61B 17/32* (2006.01)
(52) U.S. Cl.
USPC .............................................. 606/81; 606/80
(58) Field of Classification Search .............. 606/79–81, 606/91, 171, 180; 433/144, 165; 407/54, 407/62
See application file for complete search history.

(56) References Cited

U.S. PATENT DOCUMENTS

| | | | | | |
|---|---|---|---|---|---|
| 1,916,874 | A | * | 7/1933 | Wilhelm | 408/227 |
| 2,910,978 | A | * | 11/1959 | Urist | 623/22.21 |
| 4,662,891 | A | * | 5/1987 | Noiles | 623/22.31 |
| 6,723,102 | B2 | * | 4/2004 | Johnson et al. | 606/79 |
| 2006/0217730 | A1 | * | 9/2006 | Termanini | 606/81 |

FOREIGN PATENT DOCUMENTS

| | | |
|---|---|---|
| DE | 197113620 U | 7/1971 |
| DE | 8709738 U1 * | 9/1987 |
| DE | 198709738 U | 11/1987 |
| DE | 4439410 A1 | 5/1996 |
| DE | 102005031402 A1 | 1/2007 |
| EP | 1226785 A1 | 7/2002 |
| WO | WO 02102254 A2 | 12/2002 |
| WO | WO 03068078 A1 | 8/2003 |
| WO | WO 03094739 A2 | 11/2003 |
| WO | WO 2004100804 A1 | 11/2004 |
| WO | WO 2005041786 A1 | 5/2005 |

OTHER PUBLICATIONS

PCT International Search Report and Written Opinion dated Apr. 6, 2009.
UK Search Report date of search Apr. 8, 2008.

* cited by examiner

*Primary Examiner* — Todd Manahan
*Assistant Examiner* — Jessica Weiss

(57) ABSTRACT

An instrument for removing tissue from a bone to create a cavity which is approximately circular in outline in which tissue within a predetermined region within the circular outline is left relatively undisturbed. The instrument includes a rotational drive unit which oscillates through an angle $\alpha$. A cutting head can be connected to the drive unit to cause the head to rotate.

15 Claims, 2 Drawing Sheets

FIG. 1
Prior Art
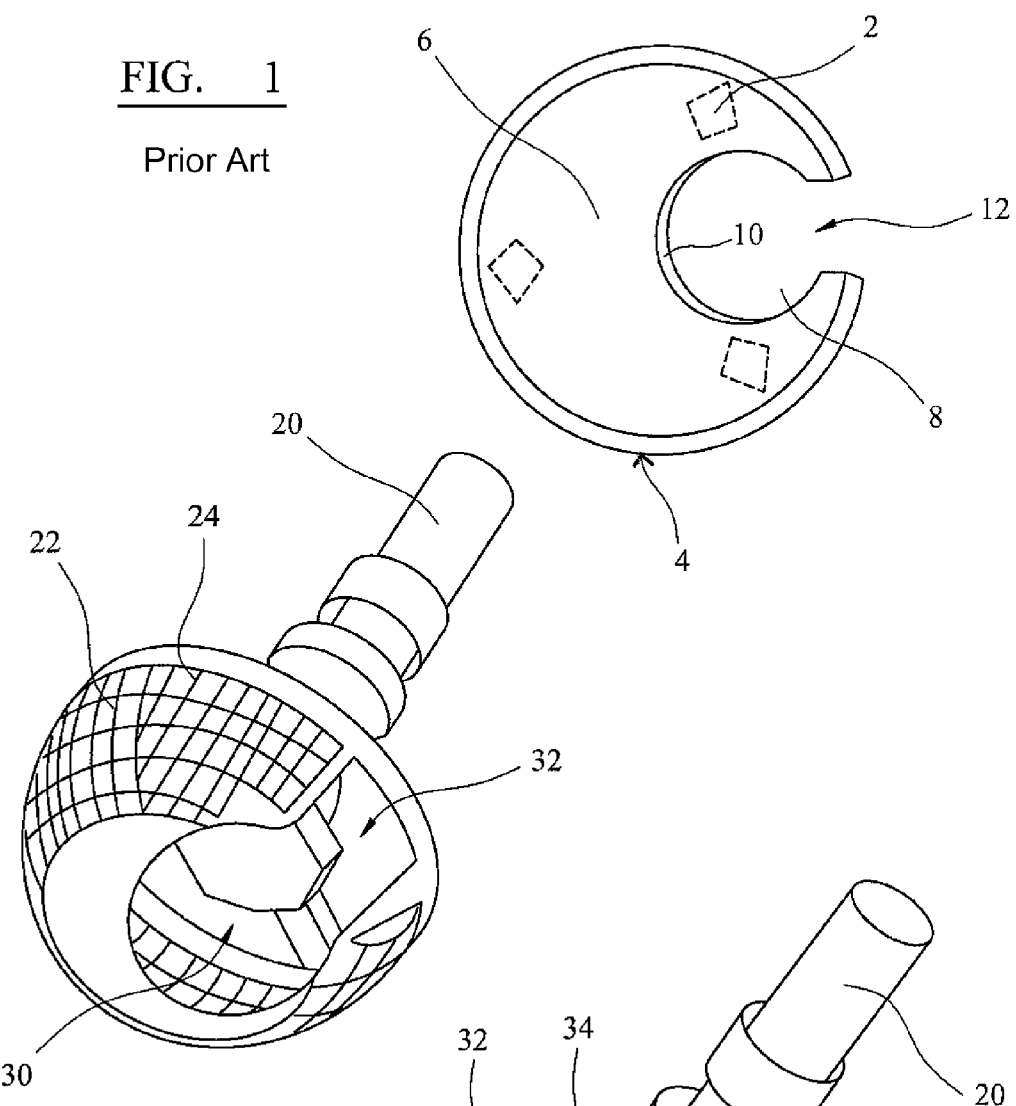
FIG. 2
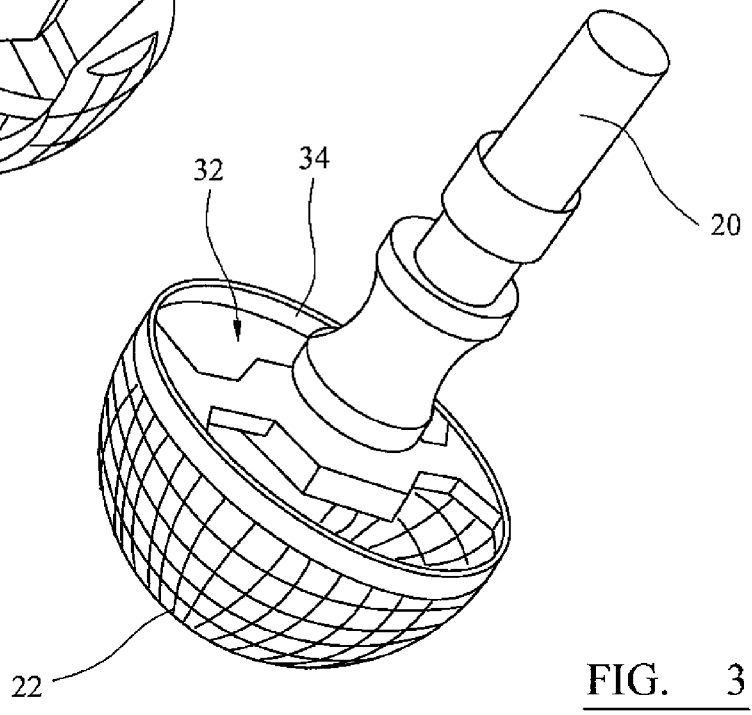
FIG. 3

INSTRUMENT FOR REMOVING BONE TISSUE

CROSS REFERENCE TO RELATED APPLICATION

This application is a National Stage application claiming the benefit under 35 U.S.C. 371 of International Patent Application PCT/GB2008/004098, filed Dec. 12, 2008.

BACKGROUND OF THE INVENTION

This invention relates to an instrument for removing tissue from a bone to create a cavity.

The acetabular component of common hip joint prostheses comprises a part-spherical shell which can be implanted in the patient's acetabulum. Generally the shell is formed from a metallic material. A liner component is fitted to the shell. The liner component is formed from a polymeric material such as an ultrahigh molecular weight polyethylene (UHM-WPE) and provides the bearing surface for articulation with the convex head of a femoral component.

U.S. Pat. No. 2,910,978 discloses an acetabular component which has a notch formed in it. The notch has a rounded portion towards the pole of the component, and a narrower neck portion which extends from the rounded portion to the peripheral edge of the component. The notch allows fat pad tissue in the acetabular fossa to be preserved when the acetabulum is prepared to receive the prosthesis component. This can promote lubrication of the joint during articulation.

BRIEF SUMMARY OF THE INVENTION

The present invention provides an instrument for removing tissue from a bone to create a cavity which is approximately circular in outline in which tissue within a predetermined region within the circular outline is left relatively undisturbed, using an oscillating cutting head with a recess in its external surface whose shape corresponds to that of the said pre-determined region, in which the angular extent of the recess in the cutting head is reduced compared with the shape of the predetermined region to an extent which corresponds to the angle $\alpha$.

Accordingly, in one aspect, the invention provides an instrument for removing tissue from a bone to create a cavity which is approximately circular in outline in which tissue within a predetermined region within the circular outline is left relatively undisturbed, which comprises:

a. a rotational drive unit which oscillates through an angle $\alpha$, and b. a cutting head which can be connected to the drive unit and thereby caused to rotate, having an overall external shape provided by (a) a cutting area in which the external surface of the head bears cutting formations enabling the head to cut the bone tissue when applied to it and rotated, and (b) a recess area which leaves tissue which it covers undisturbed as the cutting head is rotated in an oscillatory sense, in which the shapes of the cutting and recess areas are such that a line can be drawn on the surface of the cutting head at a constant distance from the axis about which the head rotates, traversing both the cutting and recess areas.

The shape of the recess area in the cutting head can be such that its angular extent is reduced compared with the shape of the predetermined region to an extent which corresponds to the angle $\alpha$. The recess area in the cutting head ensures that tissue remains undisturbed because of the oscillatory movement which is imparted to the head by the drive unit.

Preferably, the recess area of the cutting head comprises:
a. a generally rounded portion towards the pole of the head,
b. a throat portion which extends from the rounded portion towards the peripheral edge of the head and whose width measured in a plane which is perpendicular to the polar axis of the head is smaller than the maximum width of the rounded portion measured parallel to the width of the throat portion.

The recess area in the cutting head can include an elliptical portion. The elliptical portion will be arranged so that the major axis of the ellipse is approximately coplanar with the axis about which the head is rotated by the drive unit (the polar axis). The minor axis of the ellipse can then lie in a plane which is approximately perpendicular to the polar axis. The oscillatory drive imparted to the head by the drive unit will lead to the formation of an area of undisturbed tissue is approximately elliptical but with a smaller eccentricity than the elliptical recess in the cutting head, or is approximately circular.

The recess area in the cutting head can include a throat portion which extends at least partially between the polar axis and the circumferential edge of the cutting head. Preferably, the width of the throat portion is approximately constant over at least most of its length, for example at least about 50% of its length, more preferably at least about 60%, especially at least about 70%, for example at least about 80%, measured from the edge of the rounded portion to the opposite end of the throat portion.

The instrument of the invention enables a cavity to be created in a bone using a powered oscillating drive, with control over the shape of the pre-determined region in which tissue is left relatively undisturbed.

The predetermined region in which tissue is left relatively undisturbed can comprise both a rounded portion towards the pole of the acetabular cavity, and a throat portion which extends from the rounded portion towards the edge of the acetabular cavity. This can allow the fat pad tissue in the fossa region of the acetabulum to be preserved, providing the possibility of enhanced lubrication of the implanted prosthesis after implantation. To this end, the recess in the surface of the cutting head can comprise a generally rounded portion towards the pole of the head, and a throat portion which has a smaller circumferential extent than the rounded portion and which extends from the rounded portion towards the peripheral edge of the surface.

Preferably, the rounded portion of the recess in the cutting head has an approximately elliptical shape when viewed from above, with the major axis of the ellipse extending generally circumferentially on the surface of the head, approximately coplanar with the polar axis, and the minor axis of the ellipse extending generally circumferentially on the surface of the head in a plane which is approximately perpendicular to the polar axis. A cutting head with a elliptical recess can be used to form a cavity in which the rounded portion is approximately elliptical but with a smaller eccentricity than that of the recess in the cutting head, or even is approximately circular Preferably, the angle subtended at the pole of the cutting head by the rounded portion of the recess at its widest point is at least about 85°, more preferably at least about 110°, especially at least about 125°. Preferably, the angle subtended at the pole of the cutting head by the rounded portion of the recess at its widest point is not more than about 175°, more preferably not more than about 165°.

Preferably, the angle subtended at the pole of the cutting head by the throat portion of the recess at the end of the throat portion which is furthest from the pole is at least about 15°, preferably at least about 20°, for example at least about 25°. Preferably, the angle subtended at the pole of the cutting head by the throat portion of the recess at the end of the throat portion which is furthest from the pole is not more than about 50°, preferably not more than about 40°, for example not more than about 35°.

The side walls of the throat portion should be arranged to provide the desired shape for the region of undisturbed tissue. When the region of undisturbed tissue in the throat portion is desired to have sides which are parallel, the side walls of the throat portion of the cutting head can converge towards a point which is generally towards the pole of the head. Preferably, the angle between the side walls is approximately equal to the angle through which the cutting head oscillates when in use. For example, it can be preferred for the difference between the angle between the side walls and the angle through which the cutting head oscillates when in use to be not more than about 10°, more preferably not more than about 7°, especially not more than about 5°, for example not more than about 2°.

Preferably, the ratio of the major axis to the minor axis is at least about 1.05, more preferably at least about 1.1, especially at least about 1.15, for example about 1.2. The said ratio will generally be not more than about 2.5, for example not more than about 2.0.

Preferably, the ratio of the maximum width of the rounded portion when viewed from above to the width of the throat portion at its widest point (which will frequently be at the end of the throat portion which is remote from the rounded portion) is at least about 1.2, preferably at least about 1.4. Preferably, the ratio of the maximum width of the rounded portion when viewed from above to the width of the throat portion is not more than about 2.0, preferably not more than about 1.7.

The recess in the surface of the cutting head can comprise an approximately circular portion which is centred approximately on the pole of the head. Accordingly, when the head is applied to the surface of a bone and is rotated about its axis, bone is cut as a result of the action of the formations against the bone, leaving a circular region of bone adjacent to the polar recess in the cutting head generally intact. Preferably, the cutting formations are provided on the surface of the cutting head over an area which extends from the recess beyond the equator of the cutting head, and in which the angle subtended at the centre of the cutting head between the polar axis and a radius which connects the cutting formation which is furthest from the polar recess and the centre of the cutting head is at least about 120°. Preferably, the angle subtended by the recess at the centre of the cutting head is at least about 30°. Preferably, the angle subtended by the recess at the centre of the cutting head is not more than about 65°.

Preferably, the instrument includes a connector shaft by which the cutting head can be connected to a drive unit, the connector shaft being capable of being connected to the connector on the cutting head, and having non-aligned first and second shaft parts which are arranged so that rotational drive can be transmitted from a drive unit to the cutting head through a non-zero angle.

A recess in the surface of the head which includes an approximately circular portion which is centred approximately on the pole of the head, can include a throat portion which extends from the circular portion towards the peripheral edge of the surface.

Details of an instrument for removing tissue from a bone to create a cavity, which comprises an approximately spherical body having cutting formations in its external surface for cutting a bone, the body having a connector by which it can be connected to a drive by which it can be rotated about an axis, the body having a recess in it at the pole, opposite the connector, so that, when the instrument is applied to the surface of a bone and is rotated about its axis, bone is cut as a result of the action of the formations against the bone, and a circular region of bone adjacent to the polar recess in the body remains generally intact, are disclosed in an international patent application which claims priority from UK patent application no. 0725024.4, title "Instrument for removing tissue".

The recess in the cutting head can extend to the peripheral edge of the cutting head so that the recess is open at that edge. The recess in the cutting head can be closed at the peripheral edge of the cutting head, for example by a thin strip of the material of the cutting head. For example, a reinforcing rim can extend continuously around the entire periphery of the cutting head including adjacent to the recess. This can help to ensure that the cutting head is appropriately supported to withstand the forces to which it is exposed when in use.

The recess can be a blind recess so that, in the region of the recess, the cutting head has an external surface but the surface is recessed relative to the surface in the adjacent regions of the cutting head. Especially when the cutting head is hollow, the recess can be open so that it communicates directly with the interior of the cutting head.

Preferably, the cutting formations are arranged so that bone tissue is cut when the cutting head is rotated in both rotational directions.

The cutting formations can comprise a plurality of sharp ridges extending generally between the pole and the peripheral edge of the cutting head. When the cutting head is hollow, the cutting formations can comprise a plurality of openings which extend through the cutting head, each defined by one or more raised lips, each having a cutting edge (in the manner of the cutting formations on a grating device such as might be used in food preparation). Such a cutting head can be arranged to cut tissue when the head is rotated in both rotational directions by having the cutting edges of the raised lips facing in two opposite directions. Such oppositely facing cutting edges can be provided on a common opening in the cutting head. First and second sets of openings can be provided, in which the cutting edges on the openings of the first set face in a direction which is opposite to that of the cutting edges on the openings of the second set.

Preferably, the cutting head has discharge formations in its external surface which facilitate discharge of cut bone debris from the space between the external surface of the cutting head and the surface of the bone. For example, the discharge formations can comprise grooves formed in the external surface of the cutting head. When the cutting head is hollow, the discharge formations can comprise openings which extend through the cutting head.

Cutting formations and discharge formations which can be incorporated in the cutting head of the instrument of the invention are known from existing bone cutting devices, especially for preparing a cavity in the acetabulum and also for preparing bone in other surgical procedures.

The cutting head will usually have a rotationally symmetrical shape (apart from the portion of the cutting head in which the recess is provided). Generally, the overall shape of the cutting head will be approximately part-spherical. However, it might be that the shape will deviate from spherical, for example by varying the radius of the head slightly between the pole of the head and its peripheral edge. The size of the cutting head will be selected according to the desired size of the cavity in the acetabulum and therefore the size of the component of the hip joint prosthesis which is to be implanted in the prepared cavity. The diameter of the cutting head will usually be at least about 30 mm. The external diameter of the cutting head will usually be not more than about 80 mm. Examples of sizes of the cutting head include 44 mm and 70 mm.

The cutting head can include features by which it can be fastened to the rotational drive unit. In a preferred embodiment, the features can be provided on a bar which extends across the cutting head on the face which is opposite to the bone engaging surface thereof. The bar can be provided at the peripheral edge of the cutting head, which can be particularly preferred when the head has a reinforced rim. The bar can however be recessed within the head. The bar can engage the rotation drive unit using features such as hooks, retractable pins, bayonet type formations and the like. Suitable features for fastening the cutting head of a bone-cutting reamer device to a drive unit are known from existing surgical instruments.

The cutting head can be made from materials which are commonly used in the manufacture of surgical instruments. It will often be preferred to make the cutting head from a selected stainless steel which is suitably biocompatible, which can withstand the forces imposed on it when in use, and which lends itself to manufacture using conventional processing techniques.

Preferably, the oscillating rotational drive unit is powered. It can comprise a powered rotational drive, in combination with an adaptor which converts the single direction rotational drive into bi-directional oscillating drive. Suitable adaptors are known, for example as disclosed in GB-1302176, and can be obtained from the Gunson division of The Tool Connection Limited under the trade mark Eezilap.

The shape of the recess in the cutting head will be chosen having regard to the shape of the tissue within the cavity in the bone which is to be left relatively undisturbed and to the angle through which the cutting head oscillates. The angle (measured between the extremes of the oscillation) will usually be at least about 5°, preferably at least about 10°, more preferably at least about 20°. The angle will usually be not more than about 60°, preferably not more than about 45°, for example about 30°.

BRIEF DESCRIPTION OF THE DRAWINGS

Embodiments of the invention will now be described by way of example with reference to the accompanying drawings, in which:

FIG. 1 is an isometric view of the acetabular component of a hip joint prosthesis.

FIG. 2 is an isometric view of the instrument of the invention, comprising a drive unit and a cutting head.

FIG. 3 is another isometric view of the instrument which is shown in FIG. 2.

DETAILED DESCRIPTION OF THE INVENTION

Figure 4:
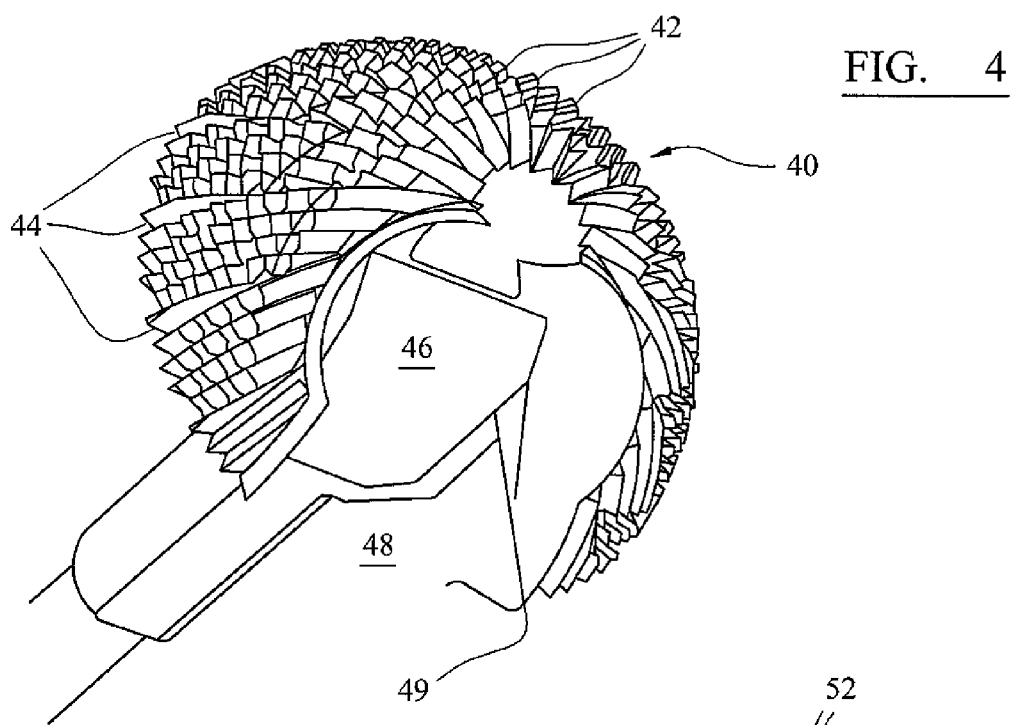
FIG. 4 is an isometric view of another embodiment of the instrument of the invention.

Referring to the drawings, FIG. 1 shows an acetabular component of a hip joint prosthesis which comprises a part-spherical shell 2 having a bone engaging surface 4 and an internal bearing surface 6. The shell is formed from a metal such as a stainless steel or a cobalt chromium molybdenum alloy as is known. The bearing surface can be provided by the metal material of the shell by suitable finishing. The bearing surface can be provided by an additional liner component (not shown) which is formed from a suitably low friction material such as UHMWPE for articulation with a metal convex head of the femoral component of the joint prosthesis.

The shell has a notch 8 formed in it. The notch comprises a rounded portion 10 which is close to the pole of the shell, and a neck portion 12 which extends from the rounded portion to the peripheral edge of the component.

The acetabular component which is shown in FIG. 1 can be implanted in a patient's acetabulum which has been prepared by removing bone tissue to create a part-spherical cavity, in which tissue in the portion of the cavity in which the notch is located is left relatively undisturbed (in the sense that it need not be trimmed to continue the spherical shape of adjacent tissue, or trimmed at all). This relatively intact tissue can comprise the fat pad in the fossa region of the acetabulum.

FIG. 2 shows an instrument which can be used to prepare the cavity in a patient's acetabulum to receive the implant shown in FIG. 1. The instrument comprises a drive unit 20 and a cutting head 22. The drive unit can comprises a rotational drive such as might be used conventionally in drilling and reaming steps of a surgical procedure. The drive unit can include an adaptor that converts the single direction rotational drive into bi-directional oscillating drive.

The cutting head 22 is provided by a hollow shell formed from a stainless steel of a type which is conventionally used in the manufacture of surgical instruments such as reamer heads. The shell has cutting formations formed in its external surface. In a preferred embodiment, the cutting formations are provided by a plurality of raised lips 24 which are shown schematically in the drawings, each having a pair of oppositely facing cutting edges. Such cutting edges are known in bone reamer devices and are similar to the cutting edges which are used in a grating device such as might be used in food preparation. Such a cutting head can cut tissue when the head is rotated in both rotational directions. The cutting formations are open to the interior of the hollow shell so that bone tissue which is cut by the formations can be discharged from the space between the bone tissue and the external surface of the shell.

The cutting formations can be provided by a plurality of sharp ridges extending generally between the pole and the peripheral edge of the cutting head, instead of or in combination with formations provided by raised lips as shown in the cutting head shown in FIG. 2.

The cutting head has a recess formed in it. The recess comprises a rounded portion 30 and a throat portion 32 which extends from the rounded portion towards the peripheral edge of the cutting head. The head has a reinforcing bead 34 at its peripheral edge which extends continuously around the entire edge.

The rounded portion 30 of the recess is approximately elliptical. The major axis of the ellipse extends in a direction from the pole of the head radially towards the peripheral edge. The minor axis of the ellipse extends circumferentially of the head. The ratio of the length of the major axis to the length of the minor axis is 1.2. When used with a drive unit which oscillates through an angle of ±15°, the resulting shape of the undisturbed bone tissue is approximately circular.

The dimensions of two preferred embodiments of the instrument of the invention are as follows:

| DIMENSION | mm | mm |
| --- | --- | --- |
| Radius of external surface of head | 49 | 55 |
| Major axis of ellipse of rounded portion of recess | 29.5 | 29.5 |
| Minor axis of ellipse of rounded portion of recess | 24.2 | 24.2 |
| Width of throat portion of recess at rim | 27.5 | 28.1 |
| Diameter of circular portion of undisturbed tissue | 27 | 27 |
| Width of undisturbed tissue at periphery of cavity | 16 | 16 |
| Angle of oscillation of drive unit | 30° | 30° |

The cutting head 22 has a bar extending across it at the peripheral edge. The bar is configured to engage an appropriate clamp on the drive unit, for example by means of bayonet fastener formations or by means of hooks, optionally with spring loaded pins, as is known in existing reamer devices.

FIG. 4 shows a reamer head 40 in which cutting teeth are provided in the form of a plurality of sharp ridges 42, which extend generally between the pole of the head and the peripheral edge of the cutting head. Suitable configurations of such ridges which enable the cutting head to cut bone when it is rotated are known. A series of spaces 44 are provided between groups of ridges, which can facilitate discharge of cut bone debris from the space between the external surface of the cutting head and the surface of the bone.

The cutting head has a recess formed in it, which comprises an elliptical portion 46 which is located towards the pole of the cutting head, and a throat portion 48 which extends between the elliptical portion and the peripheral edge 49 of the head.

Figure 5:
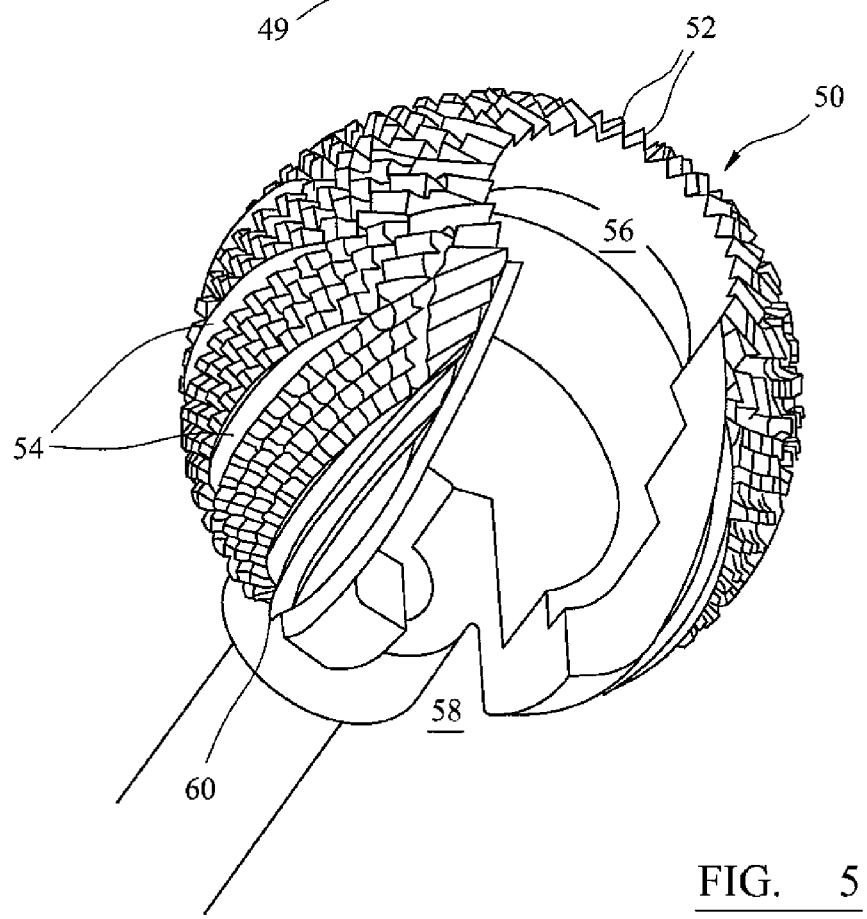
FIG. 5 is an isometric view of a further embodiment of the instrument of the invention.

FIG. 5 shows a cutting head 50 in which cutting teeth are provided in the form of a plurality of sharp ridges 52, which extend generally between the pole of the head and the peripheral edge of the cutting head. A series of spaces 54 are provided between groups of ridges, which can facilitate discharge of cut bone debris from the space between the external surface of the cutting head and the surface of the bone.

The cutting head has a recess formed in it, which comprises a circular portion 56 which is centred on the pole of the cutting head, and a throat portion 58 which extends between the elliptical portion and the peripheral edge 60 of the head. This cutting head will generally be used with a connector shaft by which the cutting head can be connected to a drive unit, the connector shaft being capable of being connected to the connector on the cutting head, and having non-aligned first and second shaft parts which are arranged so that rotational drive can be transmitted from a drive unit to the cutting head through a non-zero angle.

The invention claimed is:

1. An instrument for removing tissue from a bone to create a cavity, comprising:
    a cutting head having a generally arcuate shape, a polar axis, a pole and a peripheral edge, the cutting head being rotatable about an axis, the cutting head having an external surface, a portion of which defines a cutting area having cutting formations to enable the head to cut bone tissue when applied to bone tissue and rotated, the external surface having a recess area that includes: (a) a generally rounded portion towards the pole of the head; and (b) a throat portion that extends from the rounded portion towards the peripheral edge of the cutting head, the throat portion having a width measured in a plane that is perpendicular to the polar axis that is smaller than the maximum width of the rounded portion measured parallel to the width of the throat portion.

2. The instrument of claim 1, wherein the shapes of the cutting area and the recess area are such that a line can be drawn on the surface of the cutting head at a constant distance from the axis traversing both the cutting and recess areas.

3. The instrument of claim 1, wherein the rounded portion of the recess area has an approximately elliptical shape when viewed from above, with the major axis of the ellipse extending generally circumferentially on the surface of the head, approximately coplanar with the polar axis, and the minor axis of the ellipse extending generally circumferentially on the surface of the head in a plane that is approximately perpendicular to the polar axis.

4. The instrument of claim 3, wherein the ratio of the major axis to the minor axis is at least about 1.05.

5. The instrument of claim 1, wherein the width of the throat portion is approximately constant over at least most of its length.

6. The instrument of claim 5, wherein the ratio of the maximum width of the rounded portion when viewed from above to the width of the throat portion at its widest point is at least about 1.2.

7. The instrument of claim 5, wherein the ratio of the maximum width of the rounded portion when viewed from above to the width of the throat portion is not more than about 2.0.

8. The instrument of claim 1, wherein the recess in the surface of the cutting head comprises an approximately circular portion centered approximately on the pole of the head.

9. The instrument of claim 8, wherein the recess in the surface of the cutting head includes a throat portion that extends from the circular portion towards the peripheral edge of the surface.

10. The instrument of claim 1, wherein the cutting formations are configured so that bone tissue is cut when the cutting head is rotated in both rotational directions.

11. The instrument of claim 1, wherein the cutting formations comprise a plurality of sharp ridges extending generally between the pole and the peripheral edge of the cutting head.

12. The instrument of claim 1, wherein the cutting head has discharge formations on its external surface which facilitate discharge of cut bone debris from the space between the external surface of the cutting head and the surface of the bone.

13. The instrument of claim 12, wherein the discharge formations comprise grooves formed in the external surface of the cutting head.

14. The instrument of claim 12, wherein the cutting head is hollow, and wherein the discharge formations comprise openings which extend through the cutting head.

15. The instrument of claim 1, further comprising a drive unit connected to the cutting head.

* * * * *